US006560311B1

(12) United States Patent
Shepard et al.

(10) Patent No.: US 6,560,311 B1
(45) Date of Patent: May 6, 2003

(54) METHOD FOR PREPARING A RADIATION THERAPY PLAN (75) Inventors: David M. Shepard, Madison, WI (US); Peter Hoban, Randwick (AU); Thomas R. Mackie, Madison, WI (US); Paul J. Reckwerdt, Madison, WI (US); Gustavo H. Olivera, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/762,282
(22) PCT Filed: Aug. 6, 1999
(86) PCT No.: PCT/US99/17674
   § 371 (c)(1),
   (2), (4) Date: Mar. 15, 2001
(87) PCT Pub. No.: WO00/07668
   PCT Pub. Date: Feb. 17, 2000

Related U.S. Application Data (60) Provisional application No. 60/095,535, filed on Aug. 6, 1998.

(51) Int. Cl.⁷ .................................................. A61N 5/10
(52) U.S. Cl. ........................................ 378/65; 378/64
(58) Field of Search ......................... 378/64, 65, 97, 378/108; 600/20

(56) References Cited

U.S. PATENT DOCUMENTS

| 5,647,663 A | * | 7/1997 | Holmes ...................... 600/407 |
| 5,782,739 A | | 7/1998 | Criss et al. .................... 600/1 |
| 6,038,283 A | * | 3/2000 | Carol et al. ..................... 378/65 |
| 6,393,096 B1 | * | 5/2002 | Carol et al. ..................... 378/65 |
| 6,411,675 B1 | * | 6/2002 | Llacer ........................ 378/65 |

OTHER PUBLICATIONS

Sandham W.A. et al: "Conformal Therapy Using Maximum Entropy Optimization", International Journal of Imaging Systems and Technology, US, Wiley and Sons, New York; vol. 6, No. 1, p. 80–90; XP000620336; ISSN: 0899–9457.
Gustaffson A. et al: "A Generalized Pencil Beam Algorithm for Optimization of Radiation Therapy", Medical Physics, US, American Institute of Physics, New York; vol. 21, No. 3, p. 343–356; XP000435143; ISSN: 0094–2405.

* cited by examiner

Primary Examiner—Drew A. Dunn
Assistant Examiner—Courtney Thomas
(74) Attorney, Agent, or Firm—Quarles & Brady LLP (57) ABSTRACT A method for determining a radiation treatment plan for a radiotherapy system providing multiple individual rays of intensity modulated radiation iteratively optimized the fluence of an initial set of such rays by a function that requires knowledge of only the prescribed dose and the dose resulting from the particular ray fluences. In this way, the need to store individual dose distributions of each ray are eliminated.

18 Claims, 9 Drawing Sheets

METHOD FOR PREPARING A RADIATION THERAPY PLAN

CROSS-REFERENCE TO RELATED APPLICATIONS

This application claims the benefit of U.S. Provisional application No. 60/095/535, filed Aug. 6, 1998.

STATEMENT REGARDING FEDERALLY SPONSORED RESEARCH OR DEVELOPMENT

BACKGROUND OF THE INVENTION

The present invention relates generally to radiation therapy planning for the treatment of tumors and suitable for radiation therapy machines providing independent intensity modulated narrow beams of radiation.

Radiation therapy involves the treatment of tumorous tissue with high energy radiation according to a treatment plan. The treatment plan controls the radiation's placement and dose level so that the tumorous tissue receives a sufficient dose of radiation while the radiation to surrounding and adjacent non-tumorous tissue is minimal.

Intensity modulated radiation therapy (IMRT) treats a patient with multiple rays of radiation each of which may be independently controlled in intensity and/or energy. The rays are directed from different angles about the patient and combine to provide a desired dose pattern. Typically, the radiation source consists of either high-energy X-rays, electrons from certain linear accelerators, or gamma rays from highly focused radioisotopes such as $Co^{60}$.

Methods of producing intensity modulated rays of radiation are well known in the art and include the stop and shoot method, (Xia, P., Verhey, L. J., "Multileaf Collimation Leaf Sequencing Algorithm for Intensity Modulated Beams with Multiple Static Segments," *Medical Physics*, 25:1424–34 (1998)), the sliding window technique (Bortfeld, et al., "Realization and Verification of Three-Dimensional Conformal Radiotherapy With Modulated Fields," *Int'l J. Radiat. Oncol. Biol. Phys.*, 30:899–908 (1994)), intensity modulated arc therapy, (Yu, C. X., "Intensity-Modulated Arc Therapy With Dynamic Multileaf Collimation: An Alternative to Tomotherapy," *Physics in Medicine & Biology*, 40:1435–49 (1995)), and sequential (axial) tomotherapy, (Carol, et al., "The Field-Matching Problem as it Applies to the Peacock Three Dimensional Conformal System for Intensity Modulation," *Int'l J. Radiat. Oncol. Biol. Phys.*, 34:183–87 (1996)).

One highly accurate IMRT method uses a planar fan beam which orbits the patient in the plane of the beam to treat a single slice of the patient at a time. Prior to reaching the patient, the fan beam is passed through a multileaf collimator (MLC) consisting of a series of opaque leaves. As the radiation source rotates around the patient, the tungsten leaves move into and out of the radiation beam modulating the intensity of individual rays of the fan beam.

An intensity value for each ray of the fan beam at each angle of the fan beam about the patient and for each slice of the patient is defined by a treatment sinogram. The treatment sinogram is prepared by a physician based on a dose map indicating the amount of radiation dose and its location throughout the patient.

Preparation of a treatment sinogram from a dose map is extremely complicated. Examples include simulated annealing (Langer M. And Morrill S., "A Comparison of Mixed Integer Programming and Fast Simulated Annealing For Optimized Beam Weights in Radiation Therapy," *Medical Physics*, 23:957–64 (1996)), linear programming (Langer M. and Leong J., "Optimization of Beam Weights Under Dose-Volume Restrictions, *Int'l. J. Radiat. Oncol. Biol. Phys.*, 13:1225–60 (1987)), non-linear programming (Bortfeld et al., "Methods of Image Reconstruction From Projections Applied to Conformal Radiotherapy" *Phys. Med. Biol.*, 35:1423–34 (1990)), mixed-integer programming (Langer M. And Morrill S., "A Comparison of Mixed Integer Programing and Fast Simulated Annealing For Optimized Beam Weights in Radiation Therapy," *Medical Physics*, 23:957–64 (1996)), and iterative filtered back-projection (Holmes et al., "An Iterative Filtered Backprojection Inverse Treatment Planning Algorithm for Tomotherapy," *Int'l. J. Radiat. Oncol. Biol. Phys.*, 32:1215–1225 (1995)). Another method is the "Dynamically Penalized Likelihood" method suggested by Llacer and described in U.S. Pat. No. 5,602,892.

Many of these methods place severe burdens on computer memory. For example, in tomotherapy applications, a medium sized radiation treatment plan will often involve storing intensities of over 91,000 rays of radiation. Tracking the dose provided by these rays may require storage of more than $2.7 \times 10^{11}$ dose elements.

BRIEF SUMMARY OF THE INVENTION

The present invention provides a method and apparatus for generating treatment sinograms from dose maps.

More specifically, the present invention provides a method for optimizing a radiation treatment plan for a radiotherapy machine providing independently controlled radiation along a plurality of rays j directed towards a patient to deliver dose $D_i^d = d_{ij} w_j$ to voxels i. In a first step, a prescribed total dose $D_i^p$ at the voxels i in a treatment area is received from a physician and a fluence $w_j$ value is assigned to each ray j. An actual total dose $D_i^d$ produced at each voxel i with the assigned fluence values $w_j$ is then calculated. The fluence values $w_j$ are then modified according to an update function of the prescribed dose $D_i^p$ and the actual dose $D_i^d$ without reference to the dose per energy fluence, $d_{ij}$, delivered to each voxel by the given ray j. Finally the modified fluence values $w_j$ are used to control the radiotherapy machine.

Thus it is one object of the invention to provide a method of determining fluence values of multiple rays used in a radiation therapy session without the need to store partial dose values for each ray.

In one embodiment, the update function may be a ratio of the prescribed dose $D_i^p$ and the actual dose $D_i^d$ for each voxel i receiving radiation from the given ray j or for example:

$$w_j^{(k+1)} = w_j^k \frac{\sum_i a D_i^p}{\sum_i a D_i^{d^k}}$$

where $w_j^{(k+1)}$ and $w_j^k$ are the fluence values before and after the modification of the fluence of the rays and a is a predetermined approximation of dose per magnitude of energy fluence, $d_{ij}$.

Thus it is another object of the invention to provide a computationally simple method of modifying ray fluences such as may be rapidly executed on an electronic computer. By using an approximation of dose per energy fluence, $d_{ij}$, or dose per any magnitude related to energy fluence, the above described problems of storing and calculating partial dose are avoided.

In an alternative embodiment, the update function may be a ratio of the prescribed dose $D_i^p$ and the actual dose $D_i^d$ for each voxel i receiving radiation from the given ray j or for example:

$$w_j^{(k+1)} = w_j^k \frac{\left(\prod_i^n D_i^p\right)^{\frac{1}{n}}}{\left(\prod_i^n D_i^{d^k}\right)^{\frac{1}{n}}}$$

where $w_j^{(k+1)}$ and $w_j^k$ are the fluence values before and after the modification of step (d).

Thus it is another object of the invention to provide a function for modifying fluences of the rays to converge to produce the desired dose having no partial dose $d_{ij}$ term.

The foregoing and other objects and advantages of the invention will appear from the following description. In the description, reference is made to the accompanying drawings which form a part hereof and in which there is shown by way of illustration a preferred embodiment of the invention. Such embodiment does not necessary represent the full scope of the invention, however, and reference must be made to the claims herein for interpreting the scope of the invention.

BRIEF DESCRIPTION OF THE SEVERAL VIEWS OF THE DRAWINGS

FIG. 6a is an illustration of a DVH-based penalty system disclosed by Bortfeld et al, "Clinically Relevant Intensity Modulation Optimization Using Physical Criteria," presented at XII International Conference on the Use of Computers in Radiation Therapy, Salt Lake City, Utah, USA, 1997 (unpublished), wherein the shaded region corresponds to the zone being penalized. FIG. 6b is a generalization of the Bortfeld DVH penalty. Each region considered has a different weight in the penalization scheme.

FIG. 7b is the cumulative dose volume histogram corresponding to the dose distribution of 7a.

FIG. 8b is the cumulative dose volume histogram corresponding to the dose distribution of 8a.

DETAILED DESCRIPTION OF THE INVENTION

Radiotherapy Equipment

Whereas the present invention finds use with any radiation therapy machine capable of irradiating a patient at multiple angles with a large number of fluence controlled narrow beams of radiation in the preferred embodiment, the invention makes use of a multi-leaf collimator-type system.

Figure 1:
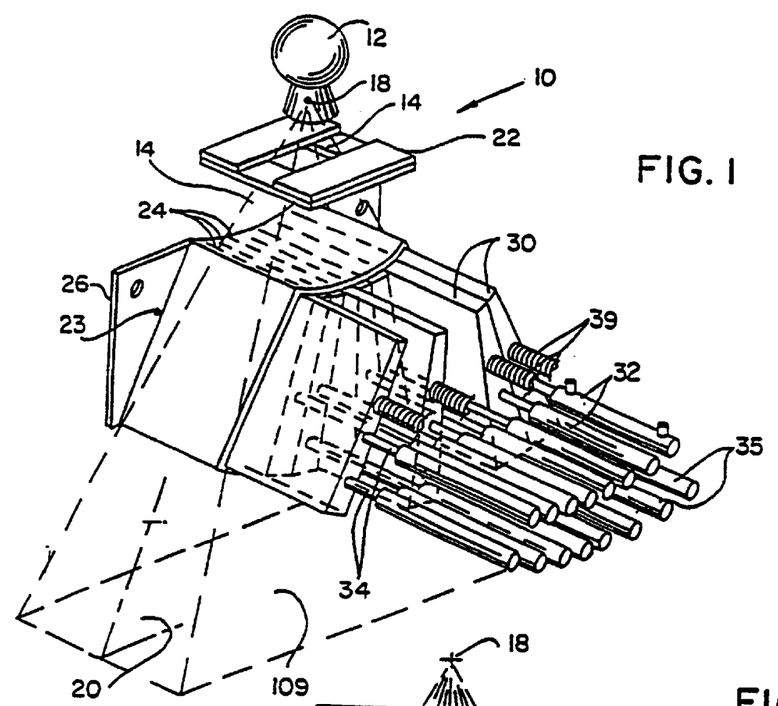
FIG. 1 is a perspective view of the shutter system assembly used in the present invention showing the shutter leaves and their associated actuators.

Referring to FIG. 1, such a radiation therapy machine 10 includes a radiation source 12 producing a generally conical radiation beam 14' emanating from a focal spot 18 and directed toward a patient 17 (not shown in FIG. 1). The conical radiation beam 14' is collimated by a rectangular opaque mask 16 constructed of a set of rectangular shutter system blades to form a generally planar radiation fan beam 14 centered about a radiation fan beam plane 20.

A shutter system 22 is centered in the radiation fan beam 14 and about the radiation fan beam plane 20 prior to the radiation beam being received by the patient 17, and includes a plurality of adjacent trapezoidal leaves 30 which together form an arc of constant radius about the focal spot 18. Each leaf is constructed of a dense radio-opaque material such as lead, tungsten, cerium, tantalum or related alloy.

The leaves 30 are held in sleeves 24 so that each leaf 30 may slide completely within its corresponding sleeve 24 to block the ray 28 associated with that sleeve 24. Preferably, the leaves 30 of the shutter system 22 subtend the entire radiation fan beam to divide the radiation fan beam into a set of adjacent slab-like rays 28 at offset angles f. When the leaf 30 blocks its corresponding ray 28, it is referred to as being in the closed state. The sleeves 24 are of ample length to permit each leaf 30 to slide out of the path of the radiation fan beam so as to leave its corresponding ray 28 completely unobstructed and yet to still be guided by the sleeve 24. In this nonlocking position, a leaf is referred to as being in the "open state".

Each leaf 30 may move rapidly between its open and closed state by means of a primary relay-like electromagnetic actuator 32 connected to the leaf 30 by a slider member 34. The fluence passed by the ray 28 may be controlled by changing the duty cycle of the movement of the leaf that is the ratio of time between which it is in the open state as opposed to the close state.

Figure 2:
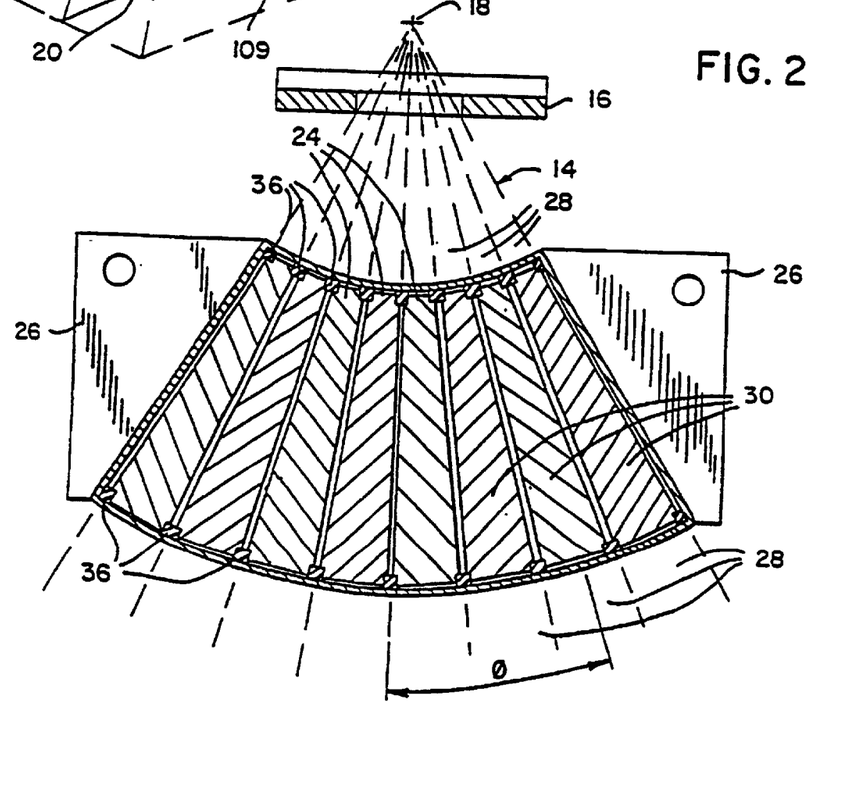
FIG. 2 is a cross section of the shutter system of FIG. 1 along line 2—2 showing the trapezoidal aspect of each shutter leaf for a radiation fan beam of radiation, and the guide rails for supporting the shutter leaves when they move.

Referring to FIG. 2, the leaves 30 are supported and guided within the sleeves 24 by guide tongues 36 fitted into grooves 38 cut along the edges of the leaves 30. The grooves 38 allow the guide tongues 36 to slidably retain the leaves 30 within the sleeves 24 during motion between the open and closed states.

Figure 3:
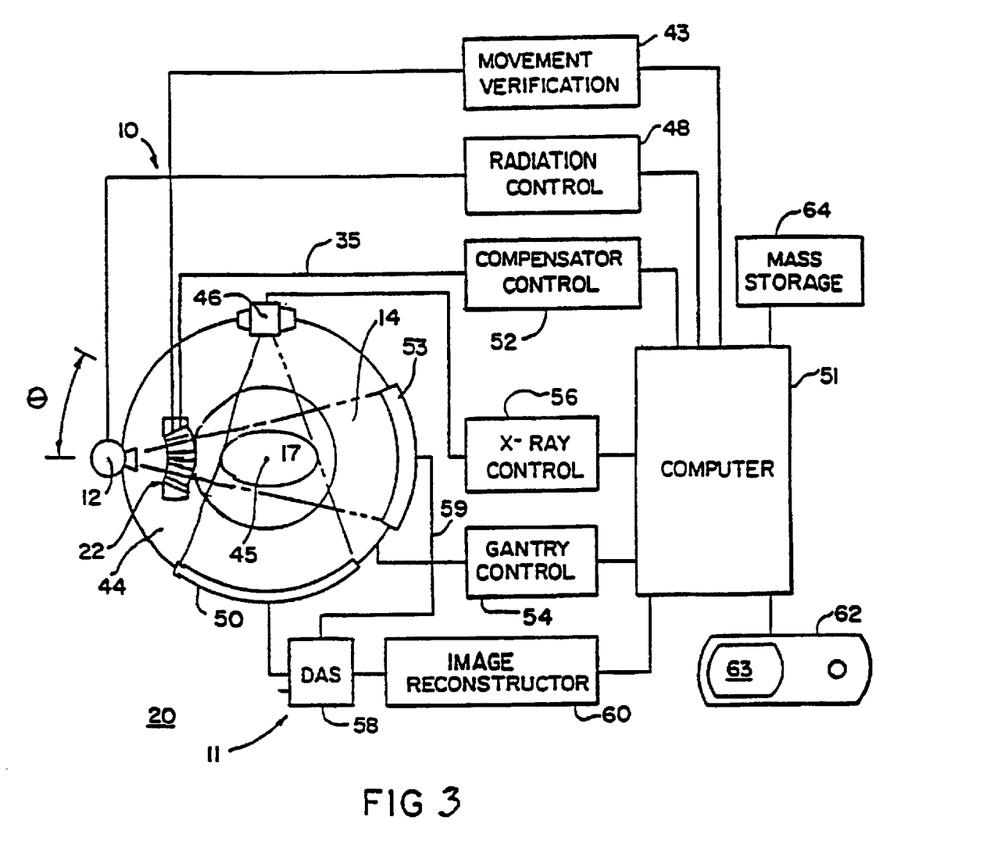
FIG. 3 is a block diagram showing the elements of a radiation therapy machine incorporating a conventional CT scanner and the shutter system of the present invention and including a computer suitable for controlling that shutter system per the present invention.

Referring now to FIG. 3, the radiation source 12 is mounted on a gantry 44, the latter rotating within the radiation fan beam plane 20 about a center of rotation 45 in the patient 17 so that the radiation fan beam 14 may irradiate a slice of the patient 17 from a variety of gantry angles θ. The radiation source 12 is controlled by a radiation control module 48 which turns the radiation beam 14 on or off under the control of a computer 51.

A shutter system control 52 directed by a timer generating desired position signals provides electrical excitation to each electromagnet to control, separately, the actuators 32 to move each of the leaves 30 in and out of its corresponding sleeve 24 and ray 38 (see also FIG. 1). The shutter system control 52 moves the leaves 30 of the shutter system 22 rapidly between their open and closed states to either fully attenuate or provide no attenuation to each ray 28. Gradations in the fluence of each ray, as needed for the fluence profile, are obtained by adjusting the relative duration during which each leaf 30 is in the closed position compared to the relative duration during which each leaf 30 is in the open position for each gantry angle.

The ratio between the closed and open states or the "duty cycle" for each leaf 30 affects the total energy passed by a given leaf 30 at each gantry angle and thus controls the average fluence of each ray 28. The ability to control the average fluence at each gantry angle permits accurate control of the dose provided by the radiation beam 14 through the irradiated volume of the patient 17 by therapy planning methods to be described below. The shutter system control 52 also connects with computer 51 to allow program control of the shutter system 22 to be described.

An optional tomographic imaging system 11 employing an x-ray source 46 and an opposed detector array 50 may be advantageously mounted on the same gantry 44 as the radiation source 12 to produce a tomographic or slice image of the irradiated slice of the patient 17 prior to radiation therapy for planing purposes or during treatment. Alternatively, such tomographic imaging may be performed on a separate machine and the slices aligned according to fiducial points on the patient 17.

A gantry control module 54 provides the signals necessary to rotate the gantry 44 and hence to change the position of the radiation source 12 and the gantry angle q of the radiation fan beam 14 for the radiation therapy, as well as for the computer tomography x-ray source 46 and detector array 50 also attached to gantry 44. Gantry control module 54 connects with computer 51 so that the gantry may be rotated under computer control and also to provide the computer 51 with a signal indicating the gantry angle q to assist in that control.

Control modules for the tomographic imaging system 11 include: x-ray control module 56 for turning on and off the x-ray source 46 and data acquisition system 58 for receiving data from the detector array 50 in order to construct a topographic image.

An image reconstructor 60 typically comprising a high speed array processor or the like receives the data from the data acquisition system 58 in order to assist in "reconstructing" a tomographic treatment image from such data according to methods well known in the art. The image reconstructor 60 may also use post-patient radiation detector signals 59 to produce a tomographic absorption image to be used for verification and future therapy planning purposes as described in more detail below.

A terminal 62 comprising a keyboard and display unit 63 allows an operator to input programs and data to the computer 51 and control the radiation therapy machine 10 and the tomographic imaging system 11 and to display images provided by the image reconstructor 60 on display unit 63.

A mass storage system 64, being either a magnetic disk unit or tape drive, allows the storage of data collected by the tomographic imaging system 11 and the post-patient radiation detector 53 for later use. Computer programs for operating the radiation therapy machine 10 will generally be stored in mass storage system 64 and laded into the internal memory of the computer 51 for rapid processing during use of the radiation therapy machine 11.

The radiation source 12 may be a linear accelerator excited in pulsed mode with the pulses in synchrony with the digital to analog converter of the data acquisition system 58 so as a set of views may be obtained during shutter opening and closing. If each projection of radiation at a given gantry angle q during radiotherapy is one second, the pulse rate of linear accelerator may be two hundred times per second providing real-time motion study of movement of the leaves 30 based on the changing fluence exiting the leaf and entering the patient 17.

During operation of the radiation therapy machine 11, the shutter system control 52 receives from the computer 51 a treatment sinogram comprising a fluence profile for each gantry angle θ. The treatment sinogram describes the intensity or fluence of each ray 28 of the radiation beam 14 that is desired for each gantry angle θ at a given position of the patient support table (not shown) as translated through the radiation beam 14.

Figure 4:
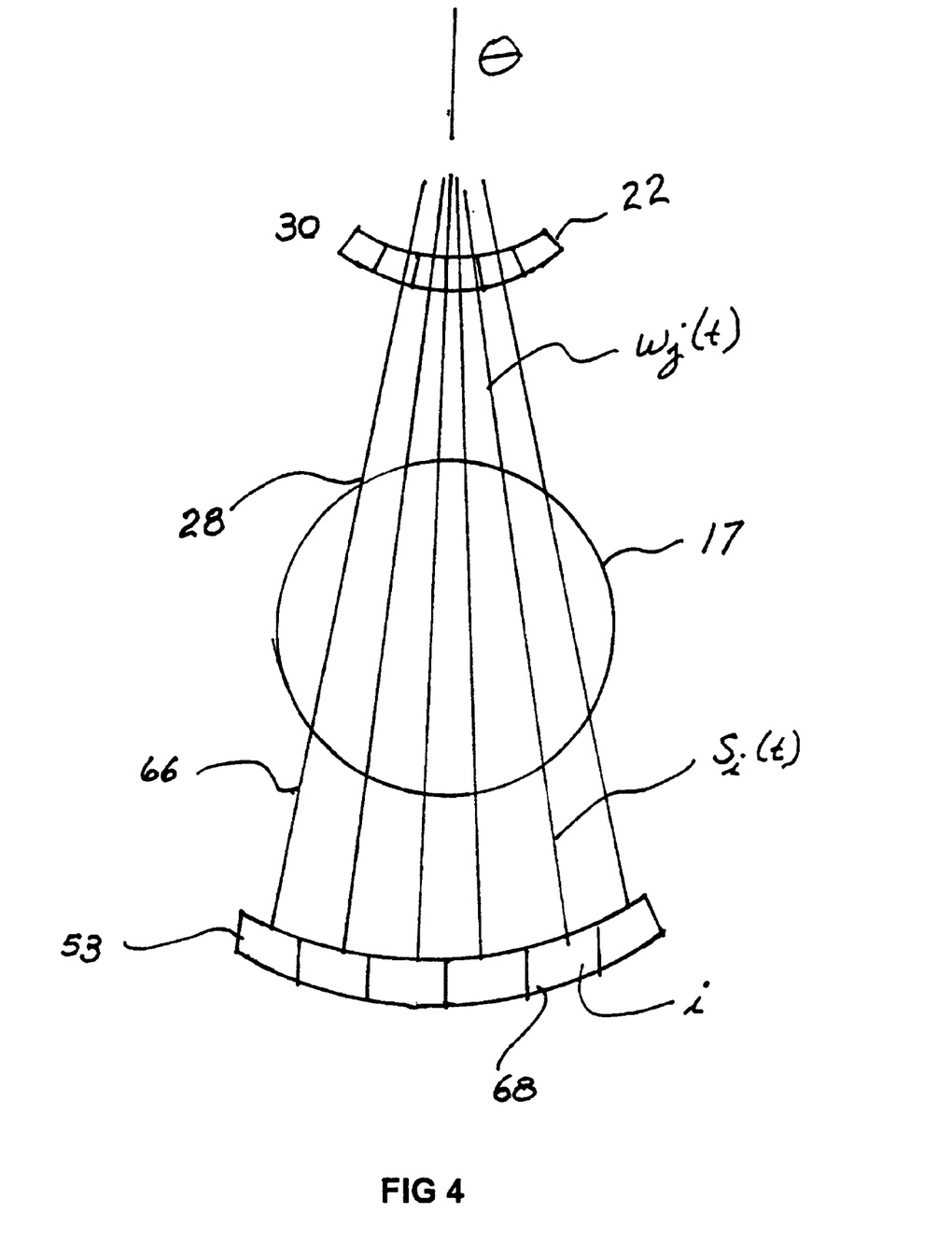
FIG. 4 is a simplified representation of the gantry of the radiation therapy machine of FIG. 3 showing variables used in the calculation of a patient model.

Referring now to FIG. 4, a shutter system provides control of a total number J of 10 rays 28 identified by index variable j=1 to J. Each ray 28 generated by the shutter system 22 passes through the patient 17 along ray center line 66 to be detected by post-patient radiation detector 53 having detector elements.

Treatment Planning

Figure 5:
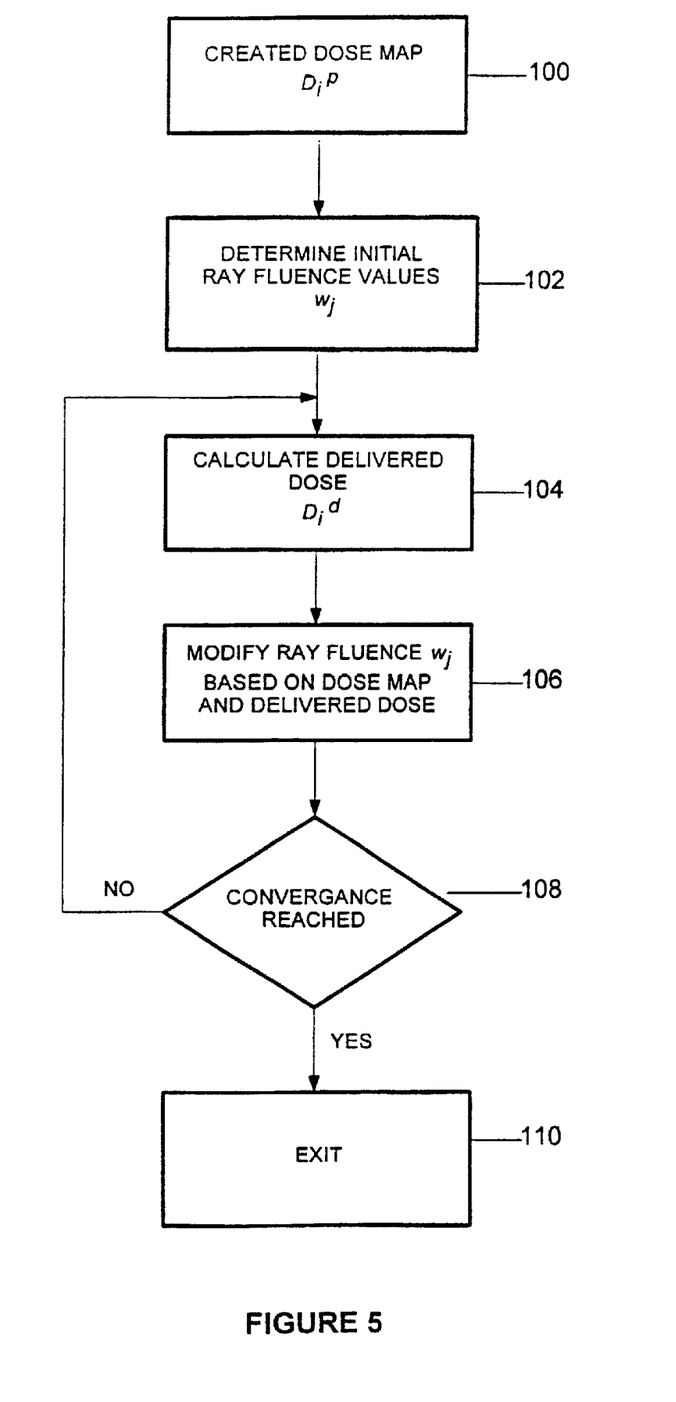
FIG. 5 is a flow diagram for the process of optimization of the ray fluence values per the present invention.

Referring to FIG. 5, the generation of the optimal radiotherapy treatment plan according to the present invention begins with the identification of a prescribed dose map $D_i^P$ providing the amount of dose desired at different voxels i within a slice as indicated by process block 100. Typically these different voxels i are grouped into areas that will include one or more areas of tumorous tissue where high dose is required and one or more areas of sensitive tissue where the dose must be limited to below a predetermined value.

The prescribed dose map $D_i^P$ is stored within the memory of the computer as an array of elements, each element holding one digital value. The method for entering the dose map $D_i^P$ may include displaying the tomographic view of the patient on the display of the terminal and manually tracing around the tumorous area using a track-ball or similar input device, as is well understood in the art. Standard area-filling algorithms may be used to transfer the dose values assigned to each trace region to the appropriate element in the array of memory representing the desired dose map. Each element of the dose map $D_i^p$ defines the dose desired at one voxel i within a slice of a patient.

A fluence value $w_j$ of each ray j of each beam at each gantry angle θ that will produce the desired dose at each voxel i must then be determined as indicated by process block 102. This process is one of iteration; an arbitrary initial fluence value $w_j$ for the rays j is selected which is then modified repeatedly until optimized values are obtained.

The closer the initial fluences $w_j$ selected for the rays j are to the final values, the faster the optimization can be completed. For this reason, in one embodiment of the present invention, a library of prior radiotherapy treatment plans is screened to select a treatment plan for treating a patient having a similar arrangement of tumorous tissue and sensitive tissues. The similarity between the patient, the previous treatment plan and the current plan will provide initial fluence values $w_j$ for the rays which are a close approximation to the rays necessary for the current radiotherapy application. The library may consist of several different treatment plans stored within a data storage system, such as a computer, and have a catalog of various treatment volumes of different shapes and sizes.

As represented by process block 104, the delivered dose $D_i^d$ that would be provided by the initial ray fluences $w_j$ is next determined by conventional techniques. As taught in U.S. Pat. No. 5,317,616 issued May 31, 1994, hereby incorporated by reference, a determination of Terma, total energy released per unit mass may be determined along each ray based on the ray's fluence and the properties of the patient. The Terma for a given voxel may be accumulated for each ray and each beam angle and then the total Terma for each voxel convolved with a precomputed scatter kernel(s) to determine dose at that voxel. The kernel(s) may represent the scatter over the range of a beam angle from different beam angles and thus in one convolution operation provide the dose calculation for all beam angles. The kernel(s) may be computed by conventional techniques such as Monte Carlo simulation. The convolution of the Terma with the scatter kernel(s) provides an accurate account of lateral scatter which is of particular importance in cases such as head and neck or tangential-field breast radiotherapy where the irradiated volume is small.

Generally, the Terma of each ray is not saved nor is the partial dose delivered to a voxel by a single ray saved, thus providing substantial memory savings.

At process block 106, the delivered dose $D_i^d$ calculated at process block 104 is compared to the prescribed dose $D_i^p$ entered at process block 100 and each ray's fluence adjusted by an update function relating to a ratio of a function of the prescribed dose $D_i^p$ over a function of the actual dose $D_i^d$ for each voxel i receiving radiation from the given ray j.

In a first embodiment, the update function is a ratio of the geometric means for the prescribed dose $D_i^p$ and the actual dose $D_i^d$ for each voxel i receiving radiation from the given ray j, and may be illustrated as follows:

$$w_j^{(k+1)} = \frac{w_j^k \left( \prod_i^n D_i^p \right)^{\frac{1}{n}}}{\left( \prod_i^n D_i^{dk} \right)^{\frac{1}{n}}} \quad (1)$$

where $w_j^{(k+1)}$ and $w_j^k$ are the fluence values before and after the modification and n is the total number of voxels. As can be seen from inspection of equation (1), only total dose values for the voxels are required and the partial doses contributed by the particular rays j are not needed and thus need not be stored as noted above.

It can be shown analytically that this first ratio update method when applied repeatedly (by repeating process blocks 104 and 106 using in each iteration of process block 104 the modified fluence values from the previous process block 106), that an objective function $O_j(\overline{w})$ tends to be optimized:

$$O_j(\overline{w}) = \sum_i \frac{1}{d_{ij}} \left\{ D_i^d \left[ \ln\left(\frac{D_i^p}{D_i^d}\right) + 1 \right] - D_i^p \right\} \quad (2)$$

which to a first order approximation is:

$$O_j^{(f)}(\overline{w}) = \sum_i \frac{1}{d_{ij}} \left\{ \frac{(D_i^p - D_i^d)^2}{D_i^p + D_i^d} \right\} \quad (3)$$

Alternatively, in a second embodiment, the update function for modifying the beam weights may be a ratio of the sum at the prescribed dose $D_i^p$ and the actual dose $D_i^d$ for each voxel i receiving radiation from the given ray j, and may be illustrated as follows:

$$w_j^{(k+1)} = w_j^k \sum_i \frac{\alpha D_i^p}{\sum_i \alpha D_i^{dk}} \quad (4)$$

where $w_j^{(k+1)}$ and $w_j^k$ are the fluence values before and after the modification and α is a predetermined approximation of the dose per energy fluence ($d_{ij}$), or dose per any magnitude related to energy fluence, of the given ray j being modified. Alternatively α may be a non-constant central axis depth dose stored and then looked up to serve as an approximation for $d_{ij}$. By not storing actual values of $d_{ij}$, the memory requirements are still significantly reduced. In the update factor, the inclusion of $d_{ij}$ would normally serve to place the greatest importance on those voxels receiving the highest dose. The approximation used may influence the rate of the conversion rate of the algorithm, but the full dose distribution determined per iteration will maintain the accuracy of a dose computation performed using the convolution/superposition technique.

It can be shown analytically that when this second update method is applied repeatedly per process block 108, (by repeating process blocks 104 and 106 using in each iteration of process block 104 the modified fluence values from the previous process block 106), that the following objective function $O_j(\overline{w})$ tends to reach optimization:

$$O(\overline{w}) = \sum_i (D_i^p - D_i^d)^n \quad (5)$$

where n is an exponent having a value of 2. In a similar approach, $O_j(\overline{w})$ may be optimized using n having value of n>2.

This equation minimizes a sum of the magnitude of the difference between the delivered doses and the prescribed doses. The convex nature of this objective function dictates that any local minimum is also the global minimum. With a convex objective function such as this, the use of stochastic optimization techniques is unwarranted.

The updating method can be further modified to make the objective function more robust. Specifically, the update function can be modified so as to apply weighting factors to each region of the patient, per the following equation:

$$w_j^{(k+1)} = w_j^k \left( \frac{\sum_{i \in T} C_T d_{ij} D_i^p + \sum_{i \in R} C_R d_{ij} D_i^p}{\sum_{i \in T} C_T d_{ij} D_i^{q(k)} + \sum_{i \in R} C_R d_{ij} D_i^{q(k)}} \right) \quad (6)$$

In this equation, $C_T$ is a weighting factor assigned to a tumor area, and $C_R$ is a weighting factor assigned to a sensitive area. T denotes the tumor volume and R indicates the sensitive area. As before the values of $d_{ij}$ may be approximated by a constant value $\alpha$ or by values looked up in a table approximating $d_{ij}$.

In its application, the penalty for overdosing a voxel in the tumor volume can be set equal to the penalty for underdosing the same voxel. It is straightforward, however, to implement weighting factors that place a greater emphasis on either underdosage or overdosage, thus producing a more clinically acceptable result.

The use of weighting factors is also applicable to sensitive structures. One possibility includes optimization where underdosed voxels are assigned a weight of zero. As a result, the voxels in the sensitive areas are only penalized if they receive a dose greater than the assigned tolerance dose.

In another embodiment, the flexibility of the iterative technique is further improved by considering a cumulative dose volume histogram (DVH) for each treatment volume. For a particularly sensitive structure, the user can specify a point on the DVH that indicates both the dose limit ($D_{max}$) and a fraction of the sensitive structure ($V_{max}$) that is permitted to exceed that limit. One possible implementation of dose volume considerations can be based upon a technique developed by Bortfeld et al, "Clinically Relevant Intensity Modulation Optimization Using Physical Criteria," presented at XII International Conference on the Use of Computers in Radiation Therapy, Salt Lake City, Utah, USA, 1997, (unpublished). With a DVH based penalty, one can obtain both a uniform target dose and a clinically acceptable dose distribution in the sensitive areas.

The DVH based penalty guides the optimization, but its specification is not an absolute constraint. A weighting factor may also be added to each DVH specification thereby increasing the penalty for a violation. By increasing the relative weighting factor assigned to a penalty, one effectively raises the importance of meeting the DVH specification.

A DVH-based penalty is particularly useful with organs that are parallel in nature. This is because with parallel coordinates, the oncologist is often willing to sacrifice a portion of the organ to obtain a favorable dose distribution in the tumor.

The present optimization technique accounts for the DVH based penalty and the computation of the update factors. Previously all of the voxels in the sensitive areas were assigned a tolerance dose. Dose volume considerations, however, only require the inclusion of a select number of sensitive area voxels for optimization.

According to this embodiment, a voxel in the sensitive structure is penalized if it receives a dose between $D_{max}$ and D'. D' is the current dose at which $V_{max}$ is exceeded. This is illustrated in FIGS. 6a and 6b. The penalized voxels represent the voxels of the sensitive areas receiving the smallest excess dose above $D_{max}$, and are penalized because they require the smallest reduction in dose in order to satisfy the DVH specification. Accordingly, the subset of penalized voxels will change with each iteration.

The penalty can be added based upon any criteria. For example, it is likely that a practitioner may choose to add a penalty if more than a certain percent of the region at risk exceeds a specified dose. Likewise, the penalty could be added to the objective function if a certain condition was not met.

Under this embodiment, the algorithm determines, once per iteration, if the DVH specification has been fulfilled. If the specification has not been met, a penalty is added to the objective function. The penalty is applied to voxels in the RAR with the smallest excess dose above $D^{plim}$. Referring to FIG. 6a, the shaded region corresponds to these voxels. The voxels are chosen because they require the smallest change in dose so as to meet the DVH specification. In this embodiment, equation (6) may be rewritten as:

$$w^{k+} = w^k \left( \frac{\sum_{i \in T} C_T d_{ij} D_i^p + \sum_{i \in R} \lambda_i^{DVH} C_R d_{ij} D_i^p}{\sum_{i \in T} C_T d_{ij} D_i^{q(k)} + \sum_{i \in R} \lambda_i^{DVH} C_R d_{ij} D_i^{q(k)}} \right) \quad (7)$$

where $\lambda_i^{DVH}$ serves as the DVH penalty. In the above example, the DVH penalty was applied to voxels located in the shaded region of the DVH shown in FIG. 6a.

A more generalized DVH penalty is also possible. For this approach, the DVH is divided in a series of dose regions. Each region has its own penalty value, $\lambda_i^{DVH}$, used to modify the DVH according to a desired plan. A typical shape of a DVH penalty applied according to this optimization method is illustrated in FIG. 6b. In this case, the optimization process is dominated by the larger $\lambda_i^{DVH}$ values. The step function shown in FIG. 6b is a representation of the pattern of weights that can be applied, and the regions where they are applied. The ordinate, however, does not represent the actual values.

The DVH based penalty does not provide a hard constraint, but is intended to only guide the optimization. A weighting factor can be added to each DVH specification thereby increasing the penalty for a violation. By increasing the relative weighting factors assigned to a penalty, one effectively raises the importance of meeting the DVH specification.

One primary advantage to the methods and apparatus of the present invention is that they provide the capability of performing large scale dose optimizations while minimizing the memory requirements of the chosen computer. The methods are also flexible, robust and capable of enhancement through the addition of weighting factors assigned to each region of the patient, or through the addition of dose volume considerations. Because of their flexibility, the present invention further benefits from its ability to work efficiently in conjunction with the convolution/superposition based dose computation.

In the methods described above, the update factor may be calculated by updating only the voxels located in the primary path of given ray j. This approach will ultimately result in quicker optimization planning for complicated radiotherapy treatments such as those used in tomotherapy.

EXAMPLE 1

A radiation treatment plan was optimized for an inverted U-shaped treatment volume surrounding a rectangular sensitive area. The U-shaped treatment volume was cut out of a 5 cm by 5 cm square, and the sensitive area was placed in the concavity of the U.

The update factor of Equation 6 was utilized to include a weighting factor for the treatment volume ($C_T$) and the sensitive area ($C_R$) of the patient. In this equation, $C_T$ and $C_R$ were set at 0.95 and 0.05, respectively.

Figure 7A:
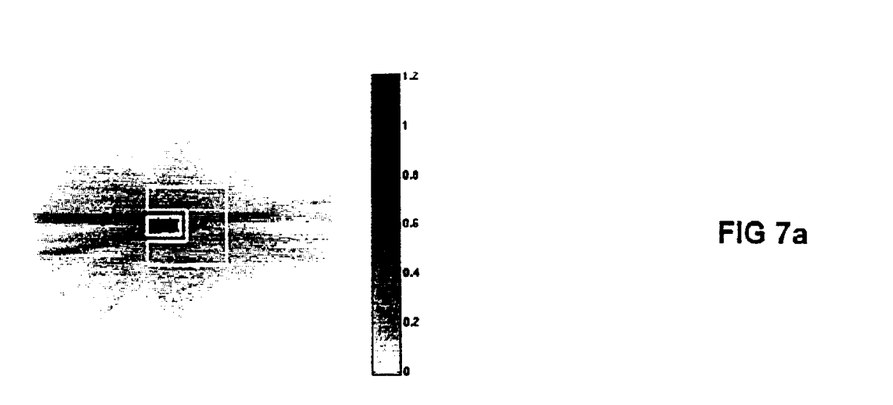
FIG. 7a is a dose distribution of a treatment plant wherein a weight of 0.95 was assigned to the treatment volume and a weight of 0.05 was assigned to the sensitive areas.
Figure 7B:
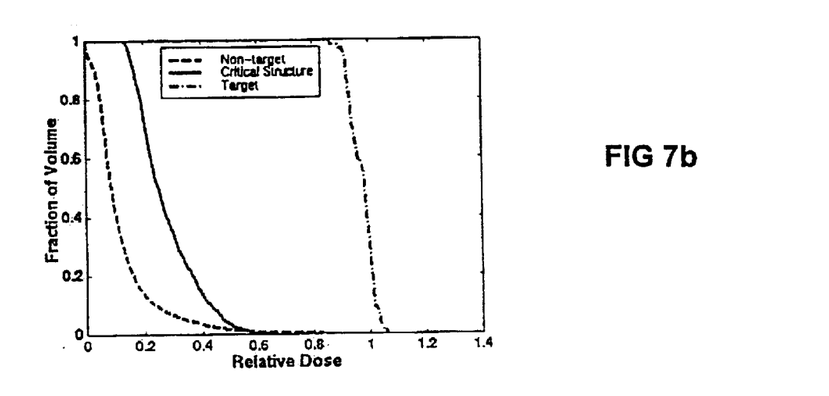

FIGS. 7a and 7b present the results from this simulation. The use of the weighting factors resulted in a significant improvement in the target dose distribution as compared with the results obtained without weighting factors. It was observed that the dose distribution in the treatment volume was improved by delivering a higher dose to a larger volume of the sensitive structure. By increasing the dose to the sensitive structure, the 90% isodose line was expanded to closely match the border of the target.

EXAMPLE 2

A radiation treatment plan was optimized according to the methods of the present invention by considering a cumulative dose volume histogram (DVH). The cumulative DVH provided a DVH-based penalty which was accounted for in the computation of the update factor during the optimization process. The update factors were modified to include a penalty if a specified voxel in the sensitive structure received a dose between $D_{max}$ and $D^*$. $D^*$ was defined as the current dose of which $V_{max}$ was exceeded.

Figure 6:
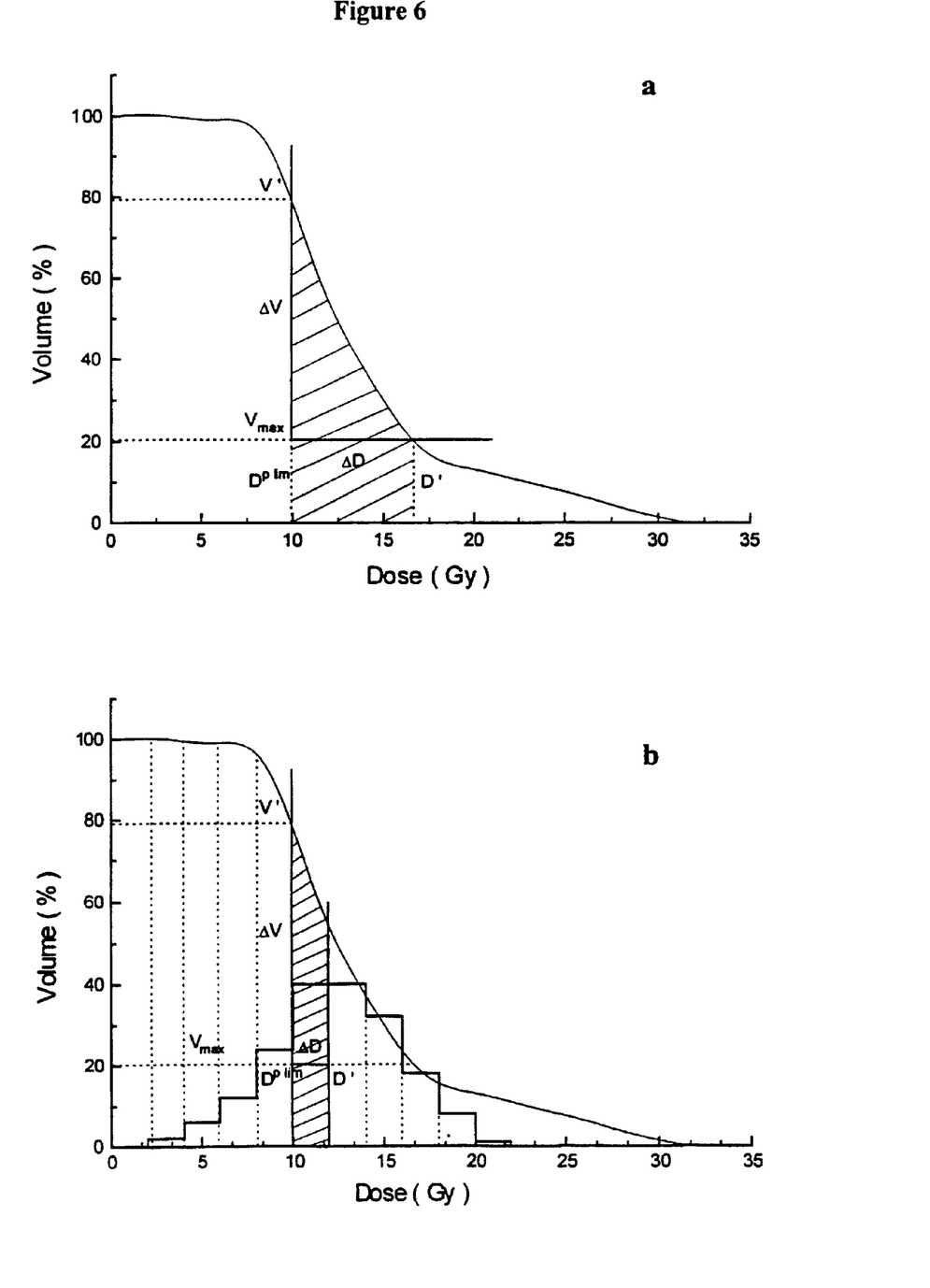
FIG. 6 includes two illustrations of a DVH-based system useful in guiding the optmization.

The characterization of the penalized voxels is illustrated in FIG. 6. The penalized voxels represent the sensitive voxels of the area receiving the smallest excess dose above $D_{max}$. These particular voxels were penalized because they required the smallest reduction in dose in order to satisfy the DVH specification. Accordingly, the subset of penalized voxels changes with each iteration.

Figure 8A:
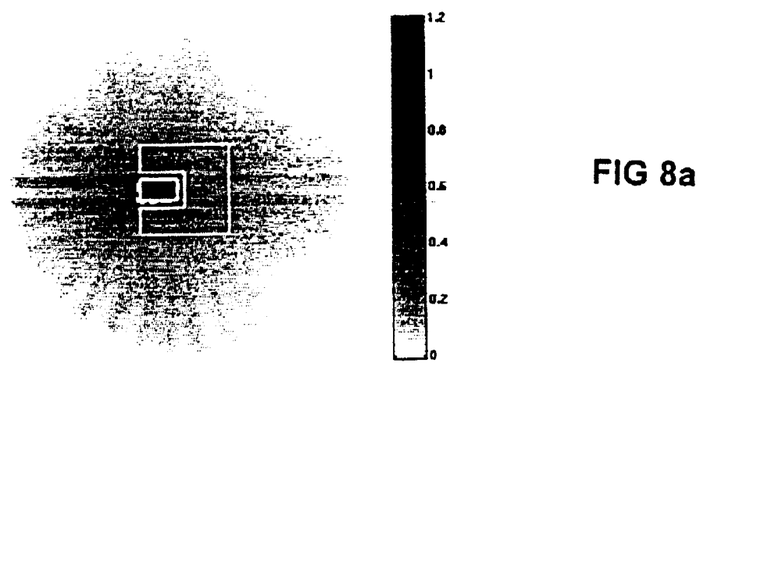
FIG. 8a is a dose distribution of a treatment plan including a DVH specification requiring a penalty to be added if more than 15% of the sensitive area exceeded a dose of 0.4.
Figure 8B:
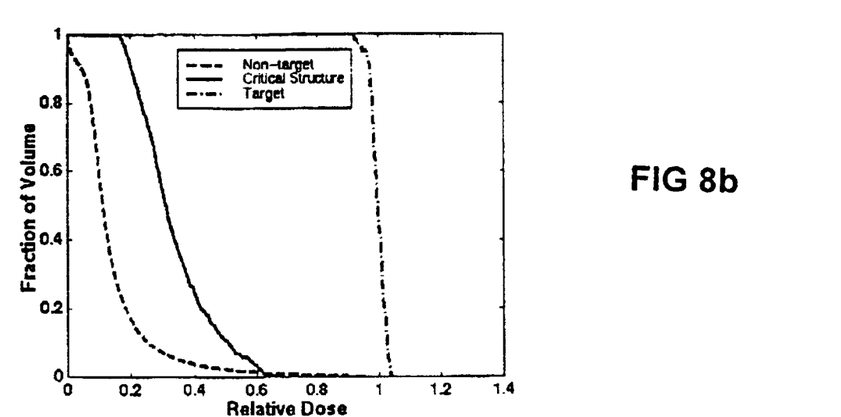

FIGS. 8a and 8b present results from an optimization process which utilized a dose volume specification in connection with Equation 5 discussed above. For the inverted U-shaped geometry, a penalty was added if more than 15% of the region at risk exceeded a dose of 0.4. As illustrated in FIG. 8a, the 90% isodose line closely matches the boundary of the treatment volume.

EXAMPLE 3

Figure 9A:
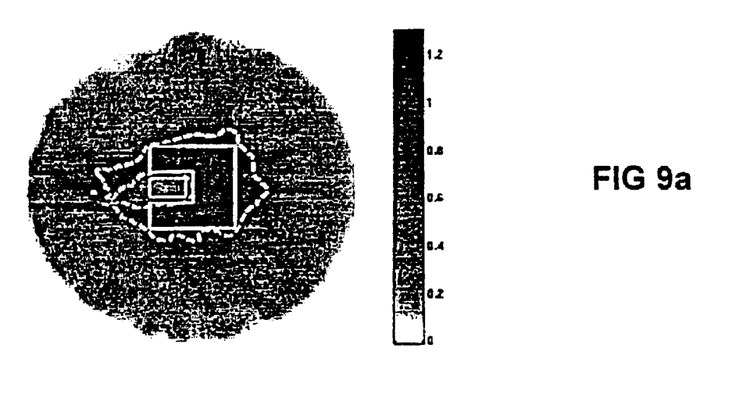
FIG. 9a is a dose distribution of a treatment plan wherein a DVH based penalty was applied if more than 25% of the sensitive area exceeded a dose of 0.1.
Figure 9B:
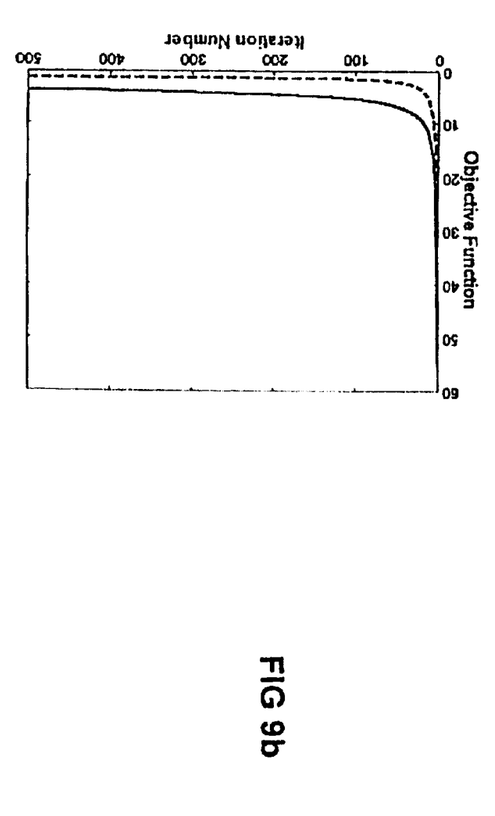
FIG. 9b is a the illustrated solution to the objective function corresponding to the dose distribution of 9a where the solid line is the sum of the squared differences between delivered and prescribed doses over all pixels in the tumor and in the sensitive area. The dash line is the value of the same computation over all tumor pixels and only those pixels in the sensitive area that are penalized.

FIG. 9 represents the results of a treatment optimization simulation involving a U-shaped treatment volume and a DVH-based penalty system. In this simulation, a penalty was added if more than 25% of the sensitive areas exceeded a dose of 0.1.

FIG. 9b represents the objective function value over the course of the optimization. The solid line depicts the value of the sum of the squared differences between the prescribed and the actual doses over the entire treatment volume and the sensitive areas. The dash line is the actual objective function that is minimized when a DVH-based penalty is employed. Specifically, it is the sum of the squared differences between the delivered dose and the prescribed dose over all voxels in the treatment volume, plus the sum of the squared differences between the delivered dose and the dose limit of the penalized voxels. Note that both of these functions decreased in value with each successive iteration.

EXAMPLE 4

DVH specifications were also tested on a simulated prostate treatment plan. In this case, the prostate was prescribed a dose of 80 Gy. The rectum DVH specifications were: (1) add a penalty if more than 15% of the rectum exceeds a dose of 25 Gy and (2) add a penalty if any voxels are above 50 Gy. The bladder DVH specifications were: (1) add a penalty if more than the 40% of the volume exceeds a dose of 27 Gy and (2) penalize all voxels over 54 Gy.

Figure 10A:
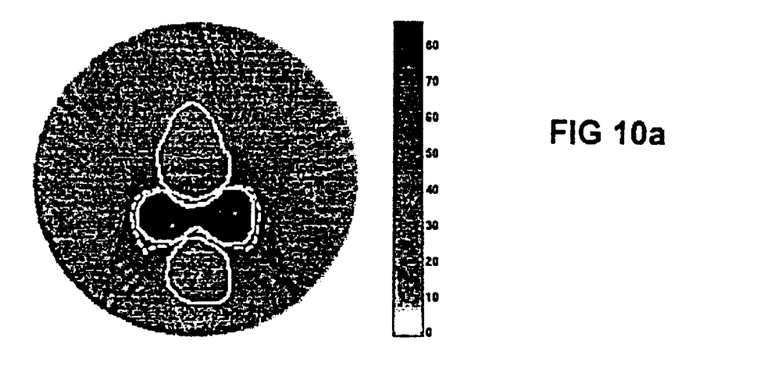
FIG. 10a is a dose distribution of a prostate treatment plan where the centrally located target includes the prostate and seminal vesicles. Above the prostate is the bladder and below is the rectum. The dash line is the 95% isodose line.
Figure 10B:
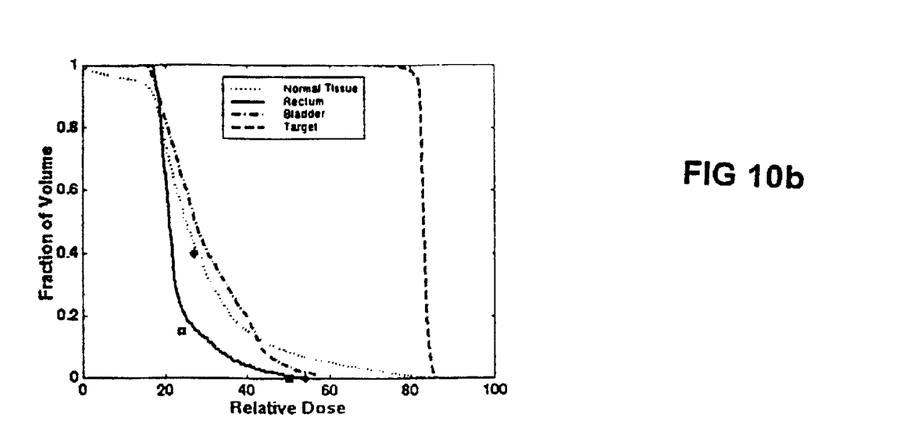
FIG. 10b is the cumulated dose volume histogram corresponding to the dose distribution of 10a. The two specifications for the rectum are shown with square DVH and the two specifications for the bladder are indicated with diamonds on the DVH.

The results of the prostate simulation are shown in FIG. 10. Note that the 95% isodose line closely matches the border of the target. The four DVH specifications are plotted in FIG. 10b.

The above description has been that of a preferred embodiment of the present invention, it will occur to those that practice the art that many modifications may be made without departing from the spirit and scope of the invention. In order to apprise the public of the various embodiments that may fall within the scope of the invention, the following claims are made.

We claim:

1. A method for optimizing a radiation treatment plan for a radiotherapy machine providing independently controlled radiation along a plurality of rays j directed towards a patient to deliver dose $D_i^d = d_{ij} w_j$ to voxels i comprising the steps:

a) identifying a prescribed total dose $D_i^p$ at the voxels i in a treatment area;

b) assigning a fluence $w_j$ value for each ray j;

c) calculating an actual total dose $D_i^d$ produced at each voxel i with the assigned fluence values $w_j$ of step (b);

d) for each given ray j, modifying the fluence value $w_j$ of step (b) according to an update function of the prescribed dose $D_i^p$ and the actual dose $D_i^d$; and e) using the modified fluence values $w_j$ to control the radiotherapy machine.

2. The method of claim 1 wherein the update function is a ratio of a function of the prescribed dose $D_i^p$ in the numerator and a function of the actual dose $D_i^d$ in the denominator for each voxel i receiving radiation from the given ray j.

3. The method of claim 2 wherein the update function is:

$$w_j^{(k+1)} = w_j^k \frac{\sum_i a D_i^p}{\sum_i a D_i^{d^k}}$$

where $w_j^{(k+1)}$ and $w_j^k$ are the fluence values before and after the modification of step (d) and $\alpha$ is a predetermined approximation of dose per magnitude of energy fluence, $d_{ij}$.

4. The method of claim 3 wherein $\alpha$ is a constant value.

5. The method of claim 3 wherein steps (b) through (d) are repeated in multiple iterations, the assigned fluence values of step (b) taking the modified fluence values of preceding step (d).

6. The method of claim 3 wherein at step (d) only the voxels i along the center line of the given ray j are considered.

7. The method of claim 1 wherein the update function is a ratio of the geometric means for the prescribed dose $D_i^p$ and the actual dose $D_i^d$ for each voxel i receiving radiation from the given ray j.

8. The method of claim 7 wherein the function is:

$$w_j^{(k+1)} = w_j^k \frac{\left(\prod_i^n D_i^p\right)^{\frac{1}{n}}}{\left(\prod_i^n D_i^{d^k}\right)^{\frac{1}{n}}}$$

where $w_j^{(k+1)}$ and $w_j^k$ are the fluence values before and after the modification of step (d).

9. The method of claim 7 wherein steps (b) through (d) are repeated in multiple iterations, the assigned fluence values of step (b) taking the modified fluence values of preceding step (d).

10. The method of claim 7 wherein at step (d) only the voxels i along the center line of the given ray j are considered.

11. The method of claim 2 wherein the update function is:

$$w_j^{(k+1)} = w_j^k \left( \frac{\sum_{i \in T} C_T a D_i^p + \sum_{i \in R} C_R a D_i^p}{\sum_{i \in T} C_T a D_i^{d(k)} + \sum_{i \in R} C_R a D_i^{d(k)}} \right)$$

where $w_j^{(k+1)}$ and $w_j^k$ are the fluence values before and after the modification of step (d), $C_T$ is a weighting factor assigned to a tumor area, $C_R$ is a weighting factor assigned to a sensitive area, and $\alpha$ is a predetermined approximation of dose per magnitude of energy fluence, $d_{ij}$.

12. The method of claim 11 where $\alpha$ is a constant value.

13. The method of claim 11 wherein steps (b) through (d) are repeated in multiple iterations, the assigned fluence values of step (b) taking the modified fluence values of preceding step (d).

14. The method of claim 11 wherein at step (d) only the voxels i along the center line of the given ray j are considered.

15. The method of claim 2 wherein the update function is:

$$w^{k+1} = w^k \left( \frac{\sum_{i \in T} C_T d_{ij} D_i^p + \sum_{i \in R} \lambda_i^{DVH} C_R d_{ij} D_i^p}{\sum_{i \in T} C_T d_{ij} D_i^{d(k)} + \sum_{i \in R} \lambda_i^{DVH} C_R d_{ij} D_i^{d(k)}} \right)$$

where $w_j^{(k+1)}$ and $w_j^k$ are the fluence values before and after the modification of step (d), $C_T$ is a weighting factor assigned to a tumor area, $C_R$ is a weighting factor assigned to a sensitive area, $\lambda_i^{DVH}$ is a penalty value assigned to each region of the patient, and a is a predetermined approximation of dose per magnitude of energy fluence, $d_{ij}$.

16. The method of claim 15 where $\alpha$ is a constant value.

17. The method of claim 15 wherein steps (b) through (d) are repeated in multiple iterations, the assigned fluence values of step (b) taking the modified fluence values of preceding step (d).

18. The method of claim 15 wherein at step (d) only the voxels i along the center line of the given ray j are considered.

* * * * *

UNITED STATES PATENT AND TRADEMARK OFFICE
CERTIFICATE OF CORRECTION

PATENT NO. : 6,560,311 B1 Page 1 of 1
DATED : May 6, 2003
INVENTOR(S) : Shepard et al.

It is certified that error appears in the above-identified patent and that said Letters Patent is hereby corrected as shown below:

Column 2,
Line 10, "Programing" should read -- Programming --.

Column 6,
Line 41, "J of 10 rays" should read -- J of rays -- (delete "10").

Column 7,
Lines 32, 33, 36 and 39, "kemel(s)" should read -- kernel(s) --.

Signed and Sealed this

Second Day of December, 2003

JAMES E. ROGAN
*Director of the United States Patent and Trademark Office*